US011138991B2

(12) United States Patent
Iwase et al.

(10) Patent No.: US 11,138,991 B2
(45) Date of Patent: Oct. 5, 2021

(54) INFORMATION PROCESSING APPARATUS AND INFORMATION PROCESSING METHOD

(71) Applicant: Sony Corporation, Tokyo (JP)

(72) Inventors: Hiro Iwase, Kanagawa (JP); Mari Saito, Kanagawa (JP); Shinichi Kawano, Tokyo (JP); Yuhei Taki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 127 days.

(21) Appl. No.: 16/500,404

(22) PCT Filed: Feb. 6, 2018

(86) PCT No.: PCT/JP2018/003881
§ 371 (c)(1),
(2) Date: Oct. 3, 2019

(87) PCT Pub. No.: WO2018/211750
PCT Pub. Date: Nov. 22, 2018

(65) Prior Publication Data

US 2020/0111505 A1 Apr. 9, 2020

(30) Foreign Application Priority Data

May 16, 2017 (JP) ............................ JP2017-096977

(51) Int. Cl.
*G16H 40/63* (2018.01)
*G06F 3/00* (2006.01)
(Continued)

(52) U.S. Cl.
CPC .............. *G10L 25/84* (2013.01); *G10L 25/60* (2013.01); *G10L 25/81* (2013.01); *G10L 2025/783* (2013.01)

(58) Field of Classification Search
CPC ................................. G16H 40/63; G06F 3/00
See application file for complete search history.

(56) References Cited

U.S. PATENT DOCUMENTS 9,704,361 B1 * 7/2017 Hazlewood ............ G08B 21/22
2012/0141964 A1 * 6/2012 Lee ........................ G16H 40/63
434/262
(Continued)

FOREIGN PATENT DOCUMENTS

JP 9-081174 A 3/1997
JP 10-020885 A 1/1998
(Continued)

OTHER PUBLICATIONS

International Search Report and Written Opinion dated Apr. 3, 2018 for PCT/JP2018/003881 filed on Feb. 6, 2018, 9 pages including English Translation of the International Search Report.

*Primary Examiner* — Shreyans A Patel
(74) *Attorney, Agent, or Firm* — Xsensus LLP

(57) ABSTRACT

[Object] To more flexibly control the affinity of a spoken utterance for a background sound in accordance with the importance degree of an information notification. [Solution] There is provided an information processing apparatus including an utterance control unit that controls an output of a spoken utterance corresponding to notification information. The utterance control unit controls an output mode of the spoken utterance on the basis of an importance degree of the notification information and affinity for a background sound. In addition, there is provided an information processing method including controlling, by a processor, an output of a spoken utterance corresponding to notification information. The controlling further includes controlling an output mode of the spoken utterance on the basis of an importance degree of the notification information and affinity for a background sound.

20 Claims, 13 Drawing Sheets

(51) Int. Cl.

| | |
|---|---|
| ***G10L 25/84*** | (2013.01) |
| ***G10L 25/60*** | (2013.01) |
| ***G10L 25/81*** | (2013.01) |
| *G10L 25/78* | (2013.01) |

(56) References Cited

U.S. PATENT DOCUMENTS

| | | | | |
|---|---|---|---|---|
| 2016/0192073 | A1* | 6/2016 | Poornachandran ...... | H04R 5/04 381/26 |
| 2019/0333361 | A1* | 10/2019 | Gullander ............... | G06T 11/00 |

FOREIGN PATENT DOCUMENTS

| | | | |
|---|---|---|---|
| JP | 11-166835 | A | 6/1999 |
| JP | 2000-244609 | A | 9/2000 |
| JP | 2003-131700 | A | 5/2003 |
| JP | 2006-048377 | A | 2/2006 |
| JP | 2009-222993 | A | 10/2009 |

* cited by examiner

FIG. 7

| | VOICE QUALITY | | | EFFECTS | PROSODY |
|---|---|---|---|---|---|
| | SEX | AGE | PITCH | SOUND QUALITY | SPEED |
| DEFAULT SPOKEN UTTERANCE | FEMALE | THIRTIES | STANDARD | HIGH | STANDARD |
| BACKGROUND SOUND | MALE | SIXTIES | LOW | LOW | SLOW |
| IMPORTANCE DEGREE: HIGH SPOKEN UTTERANCE | FEMALE | TEENS | HIGH | HIGH | FAST |
| IMPORTANCE DEGREE: LOW SPOKEN UTTERANCE | MALE | SIXTIES | LOW | LOW | SLOW |

INFORMATION PROCESSING APPARATUS AND INFORMATION PROCESSING METHOD

CROSS-REFERENCE TO RELATED APPLICATIONS

The present application is based on PCT filing PCT/JP2018/003881, filed Feb. 6, 2018, which claims priority to JP 2017-096977, filed May 16, 2017, the entire contents of each are incorporated herein by reference.

TECHNICAL FIELD

The present disclosure relates to an information processing apparatus and an information processing method.

BACKGROUND ART

In recent years, various devices have been gaining widespread use that issue information notifications or the like to users by using voices. In addition, many technologies have been developed for performing control according to the situation in which an information notification issued by an agent device as described above is outputted. For example, PTL 1 discloses technology for selecting, in a case where an information notification is issued while music is reproduced, a speech format that matches the genre of the music being reproduced.

CITATION LIST

Patent Literature

PTL 1: International Publication No. WO 2007/091475

SUMMARY OF THE INVENTION

Problem to be Solved by the Invention

However, the technology disclosed in PTL 1 selects a speech format that matches music being reproduced even in a case where the importance degree of an information notification is high. In this case, the music drowns out a spoken utterance, and a user may fail to notice an important information notification.

Accordingly, the present disclosure proposes a novel and improved information processing apparatus and information processing method that make it possible to more flexibly control the affinity of a spoken utterance for a background sound in accordance with the importance degree of an information notification.

Means for Solving the Problem

According to the present disclosure, there is provided an information processing apparatus including an utterance control unit that controls an output of a spoken utterance corresponding to notification information. The utterance control unit controls an output mode of the spoken utterance on the basis of an importance degree of the notification information and affinity for a background sound.

In addition, according to the present disclosure, there is provided an information processing method including controlling, by a processor, an output of a spoken utterance corresponding to notification information. The controlling further includes controlling an output mode of the spoken utterance on the basis of an importance degree of the notification information and affinity for a background sound.

Effects of the Invention

As described above, according to the present disclosure, it is possible to more flexibly control the affinity of a spoken utterance for a background sound in accordance with the importance degree of an information notification.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 7 is a diagram illustrating an example of an output mode controlled by an utterance control unit according to the embodiment.

MODES FOR CARRYING OUT THE INVENTION

Figure 1:
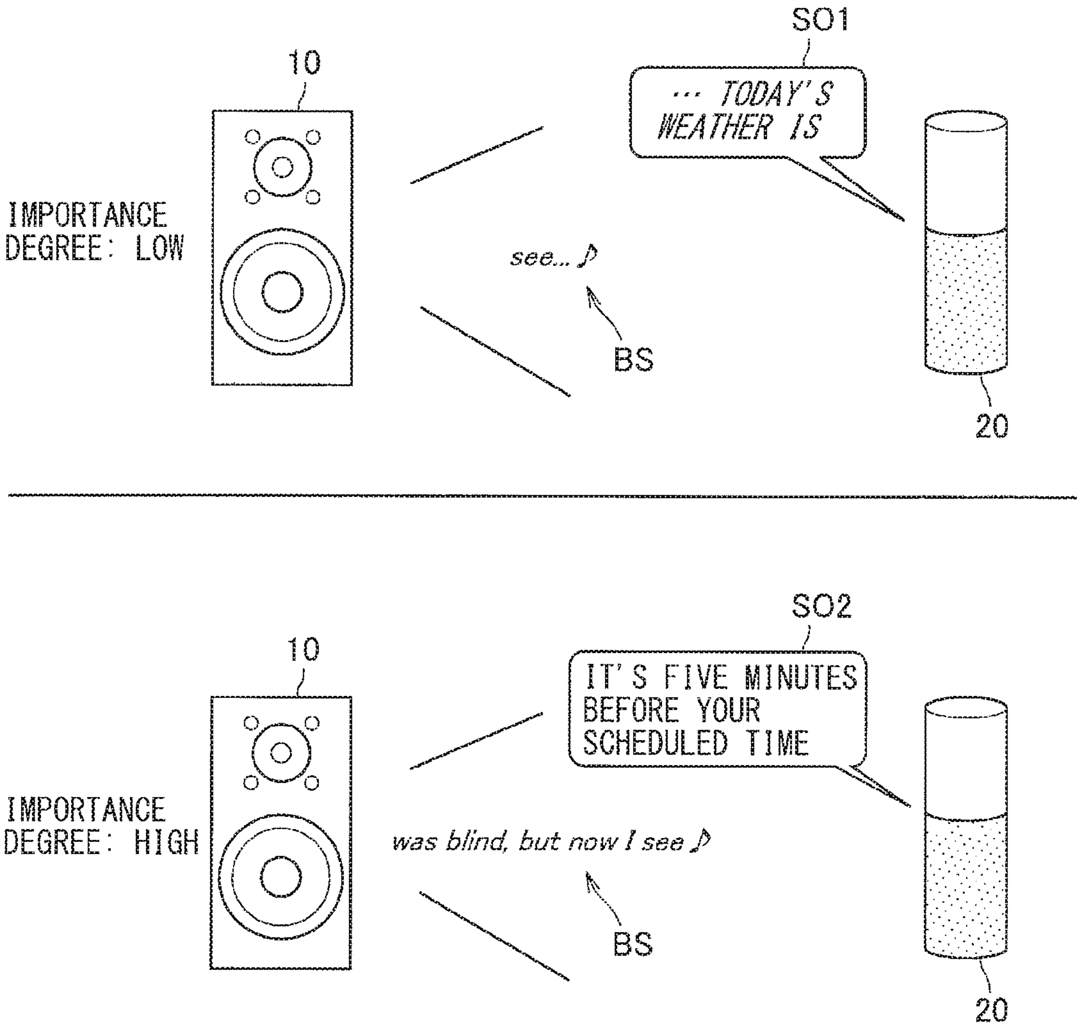
FIG. 1 is a diagram for describing an outline of a technical idea according to the present disclosure.

Hereinafter, (a) preferred embodiment(s) of the present disclosure is described in detail with reference to the appended drawings. It is to be noted that, in this specification and the appended drawings, components that have substantially the same function and configuration are denoted with the same reference numerals, thereby refraining from repeatedly describing these components.

Note that the description proceeds in the following order.

1. Embodiment
1.1. Outline
1.2. System Configuration Example
1.3. Functional Configuration Example of Reproduction Apparatus 10
1.4. Functional Configuration Example of Information Processing Terminal 20
1.5. Functional Configuration Example of Information Processing Server 30
1.6. Specific Example of Control
1.7. Flow of Control
2. Example of Hardware Configuration
3. Summary

1. Embodiment

<<1.1. Outline>>

As described above, various devices that issue information notifications or the like through spoken utterances have been gaining widespread use in recent years. Devices as described above perform information notifications in various situations. For example, information notifications are issued through spoken utterances in a situation with a background sound such as music in many cases.

However, for example, in a case where a spoken utterance is outputted while music is reproduced, a case is also assumed where the spoken utterance seriously spoils the mood of the music, or where the user fails to grasp the contents of an information notification because the spoken utterance and the singing voice compete with each other.

For this reason, in issuing an information notification through a spoken utterance, it is necessary to output, at appropriate timing, a voice that matches the background sound.

However, in a case where control as described above is performed at all times, the convenience is impaired in some cases to the contrary. For example, in a case where the importance degree of an information notification is high, the use of a voice that matches the background sound causes the information notification to be drowned out in the background sound, and arouses the concern that a user fails to notice an important information notification. It is thus desirable that the information notification issued through a spoken utterance be controlled by taking into consideration both the importance degree of the information notification and the affinity for the background sound.

The technical idea according to the present disclosure has been conceived by focusing on the points described above, and makes it possible to more flexibly control the affinity of a spoken utterance for a background sound in accordance with the importance degree of an information notification. To this end, one of the characteristics of the information processing apparatus and information processing method according to an embodiment of the present disclosure is to control an output mode of a spoken utterance on the basis of the importance degree of notification information and the affinity for a background sound.

FIG. 1 is a diagram for describing the outline of the technical idea according to the present disclosure. A reproduction apparatus 10 illustrated in FIG. 1 is an apparatus that reproduces content such as music or video, and an information processing terminal 20 is an apparatus that issues an information notification through a spoken utterance on the basis of the control performed by an information processing server 30 according to the present embodiment.

The upper portion of FIG. 1 illustrates an example of the output control of a spoken utterance in a case where the importance degree of an information notification is relatively low. In a case where the importance degree of an information notification is relatively low, the information processing server 30 according to the present embodiment is able to cause the information processing terminal 20 to output a spoken utterance SO1 in an output mode of high affinity for a background sound BS. In other words, the information processing server 30 according to the present embodiment causes the information processing terminal 20 to output the spoken utterance SO1 in an output mode that matches the background sound BS outputted from the reproduction apparatus 10.

Here, the output mode described above includes the output timing, voice quality, prosody, effects, and the like of a spoken utterance. In a case where the importance degree of an information notification is relatively low, the information processing server 30 may set voice quality, prosody, and effects similar to the vocal included in the background sound BS that is, for example, music, and control the output of the spoken utterance SO1 made by the information processing terminal 20.

Here, the voice quality described above includes the sex and height of a speaker, the pitch of a voice, and the like. In addition, the prosody described above includes speech rhythm, stress, length, and the like. In addition, the effects described above include, for example, the sound quality of a voice or various processing states brought about by signal processing.

Note that character decorations for background sounds and utterance voices in the drawings of the present disclosure indicate the voice quality, prosody, effects, and the like described above. For example, the upper portion of FIG. 1 illustrates that the spoken utterance SO1 is outputted with voice quality, prosody, or effects similar to those of the background sound BS because the character decorations for the background sound BS and the spoken utterance SO1 are the same.

In addition, in a case where the importance degree of an information notification is relatively low, the information processing server 30 is able to set output timing at which the main portion included in the background sound BS is not disturbed, and cause the information processing terminal 20 to output the spoken utterance SO1 at the output timing. Here, the main portion described above refers, for example, to the vocal portion, chorus, theme, or the like of a musical composition, or an utterance portion or an exciting portion such as the climax of a video or a game. In the case of the example illustrated in the upper portion of FIG. 1, the information processing server 30 outputs the spoken utterance SO1 not to overlap with the vocal of the background sound BS.

In this way, with respect to an information notification of a relatively low importance degree, the information processing server 30 according to the present embodiment is able to control the output mode of the spoken utterance SO1 for higher affinity for the background sound BS. In other words, the spoken utterance SO1 matches the background sound BS. The above-described function of the information processing server 30 makes it possible to issue a more natural information notification without spoiling the mood of the background sound BS such as music.

Meanwhile, the lower portion of FIG. 1 illustrates an example of the output control of a spoken utterance in a case where the importance degree of an information notification is relatively high. In a case where the importance degree of an information notification is relatively high, the information processing server 30 according to the present embodiment may cause the information processing terminal 20 to output a spoken utterance SO2 in an output mode of low affinity for the background sound BS. In other words, the information processing server 30 according to the present embodiment is able to set the output mode in which the spoken utterance SO2 is emphasized as compared with the background sound BS outputted from the reproduction apparatus 10, and cause the information processing terminal 20 to output the spoken utterance SO2.

The lower portion of FIG. 1 illustrates that the spoken utterance SO2 is outputted with voice quality, prosody, or effects that are not similar to those of the background sound BS because the character decorations for the background sound BS and the spoken utterance SO2 are different.

In addition, in a case where the importance degree of an information notification is relatively high, the information processing server 30 is able to set output timing at which the spoken utterance SO2 is emphasized as compared with the background sound BS, and cause the information processing terminal 20 to output the spoken utterance SO2 at the output timing. For example, the information processing server 30 may emphasize the spoken utterance SO2 by causing the spoken utterance SO2 to be outputted overlapping with the vocal included in the background sound BS, as illustrated in the diagram. Meanwhile, the information processing server 30 assumes that the attention of a user is not directed to the information notification, for example, in a highly exciting portion such as the main portion of the background sound BS. The information processing server 30 causes an output to be made while avoiding the main portion, thereby allowing the spoken utterance SO2 to be emphasized.

In this way, with respect to an information notification of a relatively high importance degree, the information processing server 30 according to the present embodiment is able to control the output mode for lower affinity for the background sound BS. In other words, the spoken utterance SO2 is emphasized as compared with the background sound BS. According to the above-described function of the information processing server 30, emphasizing the spoken utterance SO2 as compared with the background sound BS in the presence of the background sound BS such as music makes it possible to effectively reduce risks that a user fails to notice an important information notification.

The outline of the technical idea according to the present disclosure has been described above. Note that the above describes, as an example, the case where the background sound is content such as music reproduced by the reproduction apparatus 10, but the background sound according to the present embodiment includes various sounds such as music, an utterance, and an environmental sound. In addition, the background sound according to the present embodiment is not limited to a sound outputted from the reproduction apparatus 10, but may include various sounds that may be collected by the information processing terminal 20. A specific example of the background sound according to the present embodiment is separately described in detail.

<<1.2. System Configuration Example>>

Figure 2:
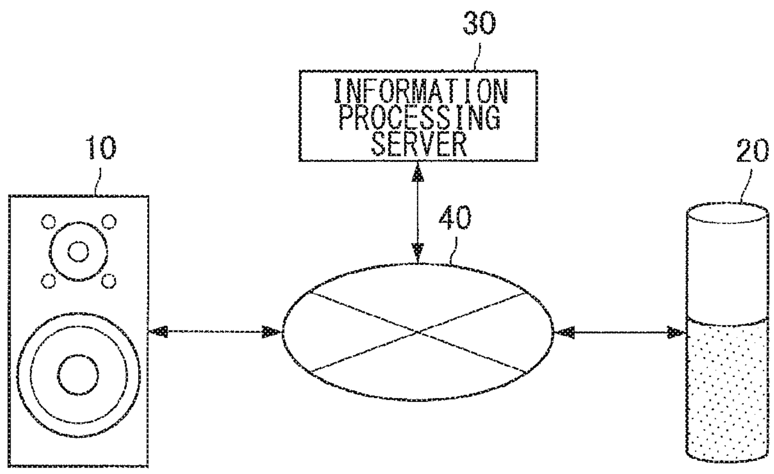
FIG. 2 is a block diagram illustrating a configuration example of an information processing system according to an embodiment of the present disclosure.

Next, a system configuration example according to the present embodiment is described. FIG. 2 is a block diagram illustrating a configuration example of the information processing system according to the present embodiment. FIG. 2 illustrates that information processing system according to the present embodiment may include the reproduction apparatus 10, the information processing terminal 20, and the information processing server 30. In addition, the reproduction apparatus 10 and the information processing server 30 are coupled to each other via a network 40, and the information processing terminal 20 and the information processing server 30 are coupled to each other via the network 40, which allows the reproduction apparatus 10 and the information processing server 30 to communicate with each other and allows the information processing terminal 20 and the information processing server 30 to communicate with each other.

(Reproduction Apparatus 10)

The reproduction apparatus 10 according to the present embodiment is an apparatus that reproduces music, a voice, and another sound corresponding to the background sound. The reproduction apparatus 10 may include various apparatuses that reproduce music content, video content, and the like. The reproduction apparatus 10 according to the present embodiment may be, for example, an audio apparatus, a television receiver, a smartphone, a tablet, a wearable apparatus, a computer, an agent apparatus, a telephone, or the like.

(Information Processing Terminal 20)

The information processing terminal 20 according to the present embodiment is an apparatus that outputs a spoken utterance on the basis of the control performed by the information processing server 30. In addition, the information processing terminal 20 according to the present embodiment has a function of collecting, as the background sounds, sounds outputted by the reproduction apparatus 10 and various sounds generated in the surroundings. The information processing terminal 20 according to the present embodiment may be, for example, a smartphone, a tablet, a wearable apparatus, a computer, an agent apparatus, or the like.

(Information Processing Server 30)

The information processing server 30 according to the present embodiment is an information processing apparatus that controls the output mode of a spoken utterance by the information processing terminal 20 on the basis of the background sound collected by the information processing terminal 20 and the importance degree of an information notification. As described above, in a case where the importance degree of an information notification is relatively low, the information processing server 30 according to the present embodiment is able to set an output mode of high affinity for the background sound, and cause the information processing terminal 20 to make a spoken utterance. In contrast, in a case where the importance degree of an information notification is relatively high, it is possible to set an output mode of low affinity for the background sound, and cause the information processing terminal 20 to make a spoken utterance.

(Network 40)

The network 40 has functions of coupling the reproduction apparatus 10 and the information processing server 30 to each other, and coupling the information processing terminal 20 and the information processing server 30 to each other. The network 40 may include public networks such as the Internet, a telephone network, and a satellite communication network, and various LAN (Local Area Networks), WAN (Wide Area Networks), and the like including Ethernet (registered trademark). In addition, the network 40 may include leased line networks such as IP-VPN (Internet Protocol-Virtual Private Network). In addition, the network 40 may include wireless communication networks of Wi-Fi (registered trademark), Bluetooth (registered trademark), and the like.

The configuration example of the information processing system according to the present embodiment has been described above. Note that the functional configuration described above with reference to FIG. 2 is merely an example. The functional configuration of the information processing system according to the present embodiment is not limited to the example. For example, the background sound according to the present embodiment is not limited to a sound outputted from the reproduction apparatus 10. Therefore, the information processing system according to the present embodiment does not necessarily have to include the reproduction apparatus 10. In addition, the functions of the reproduction apparatus 10 and the information processing terminal 20 may be implemented by a single apparatus. Similarly, the functions of the information processing terminal 20 and the information processing server 30 may be implemented by a single apparatus. It is possible to flexibly modify the functional configuration of the information processing system according to the present embodiment in accordance with the specifications and operations.

<<1.3. Functional Configuration Example of Reproduction Apparatus 10>>

Figure 3:
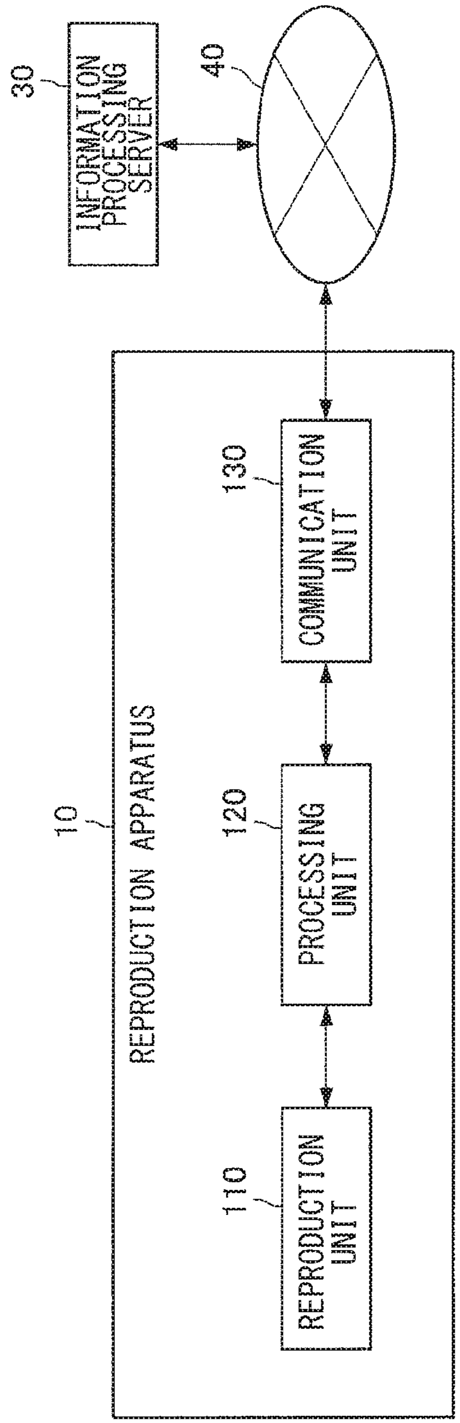
FIG. 3 is an example of a functional block diagram of a reproduction apparatus according to the embodiment.

Next, a functional configuration example of the reproduction apparatus 10 according to the present embodiment is described in detail. FIG. 3 is an example of a functional block diagram of the reproduction apparatus 10 according to the present embodiment. FIG. 3 illustrates that the reproduction apparatus 10 according to the present embodiment includes a reproduction unit 110, a processing unit 120, and a communication unit 130.

(Reproduction Unit 110)

The reproduction unit 110 according to the present embodiment has a function of reproducing music content, video content, and the like. To this end, the reproduction unit 110 according to the present embodiment includes various display devices, amplifiers, speakers, and the like.

(Processing Unit 120)

The processing unit 120 according to the present embodiment executes various kinds of processing for the reproduction unit 110 to reproduce content. The processing unit 120 according to the present embodiment is able to execute, for example, cancellation processing on a singing voice, an utterance, or the like. The cancellation processing is described below. In addition, the processing unit 120 according to the present embodiment may perform various kinds of control according to the characteristics of the reproduction apparatus 10, in addition to the processing of reproducing content.

(Communication Unit 130)

The communication unit 130 according to the present embodiment has a function of performing information communication with the information processing server 30 via the network 40. Specifically, the communication unit 130 may transmit, to the information processing server 30, information relating to content reproduced by the reproduction unit 110. In addition, the communication unit 130 may receive, from the information processing server 30, a control signal for the cancellation processing on a singing voice, an utterance, or the like.

The functional configuration example of the reproduction apparatus 10 according to the present embodiment has been described above in detail. Note that the functional configuration described above with reference to FIG. 3 is merely an example. The functional configuration of the reproduction apparatus 10 according to the present embodiment is not limited to the example. The reproduction apparatus 10 according to the present embodiment may further include a component other than those illustrated in FIG. 3. The reproduction apparatus 10 may further include, for example, an input unit or the like that receives an input made by a user. In addition, the functions of the reproduction unit 110 and the processing unit 120 may be implemented by the information processing terminal 20. It is possible to flexibly modify the functional configuration of the reproduction apparatus 10 according to the present embodiment in accordance with the specifications and operations.

<<1.4. Functional Configuration Example of Information Processing Terminal 20>>

Figure 4:
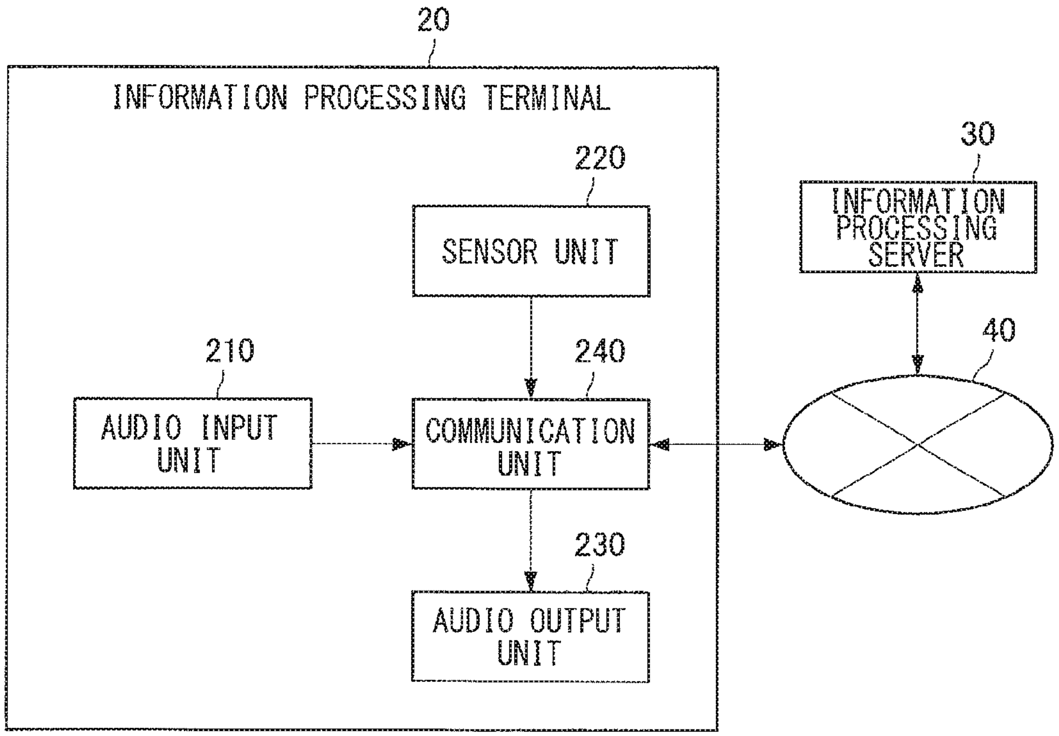
FIG. 4 is an example of a functional block diagram of an information processing terminal according to the embodiment.

Next, a functional configuration example of the information processing terminal 20 according to the present embodiment is described in detail. FIG. 4 is an example of a functional block diagram of the information processing terminal 20 according to the present embodiment. FIG. 4 illustrates that the information processing terminal 20 according to the present embodiment includes an audio input unit 210, a sensor unit 220, an audio output unit 230, and a communication unit 240.

(Audio Input Unit 210)

The audio input unit 210 according to the present embodiment has a function of collecting a background sound and an utterance made by a user. As described above, the background sound according to the present embodiment includes various sounds generated around the information processing terminal 20 in addition to a sound reproduced by the reproduction apparatus 10. The audio input unit 210 according to the present embodiment includes a microphone for collecting a background sound.

(Sensor Unit 220)

The sensor unit 220 according to the present embodiment has a function of collecting various kinds of information relating to a user and a surrounding environment. The sensor unit 220 according to the present embodiment includes, for example, an acceleration sensor, an angular velocity sensor, a geomagnetic sensor, an optical sensor, a temperature sensor, a GNSS (Global Navigation Satellite System) signal receiver, various biological sensors, and the like. The biological sensors described above include, for example, a sensor that collects information regarding a user's pulse, blood pressure, brain wave, respiration, body temperature, and the like. The sensor information collected by the sensor unit 220 according to the present embodiment may be used for the information processing server 30 to determine the importance degree of an information notification.

(Audio Output Unit 230)

The audio output unit 230 according to the present embodiment has a function of outputting a spoken utterance on the basis of the control performed by the information processing server 30. In this case, one of the characteristics of the audio output unit 230 according to the present embodiment is to output a spoken utterance corresponding to the output mode set by the information processing server 30. The audio output unit 230 includes an amplifier and a speaker for outputting a spoken utterance.

(Communication Unit 240)

The communication unit 240 according to the present embodiment has a function of performing information communication with the information processing server 30 via the network 40. Specifically, the communication unit 240 transmits the background sound collected by the audio input unit 210 and the sensor information collected by the sensor unit 220 to the information processing server 30. In addition, the communication unit 240 receives an artificial voice used for a spoken utterance from the information processing server 30.

The functional configuration example of the information processing terminal 20 according to the present embodiment has been described above in detail. Note that the functional configuration described above with reference to FIG. 4 is merely an example. The functional configuration of the information processing terminal 20 according to the present embodiment is not limited to the example. The information processing terminal 20 according to the present embodiment may further include a component other than those illustrated in FIG. 4. The information processing terminal 20 may further include, for example, a component corresponding to the reproduction unit 110 of the reproduction apparatus 10. In addition, as described above, the function of the information processing terminal 20 according to the present embodiment may be implemented as the function of the information processing server 30. It is possible to flexibly modify the functional configuration of the information processing terminal 20 according to the present embodiment in accordance with the specifications and operations.

<<1.5. Functional Configuration Example of Information Processing Server 30>>

Figure 5:
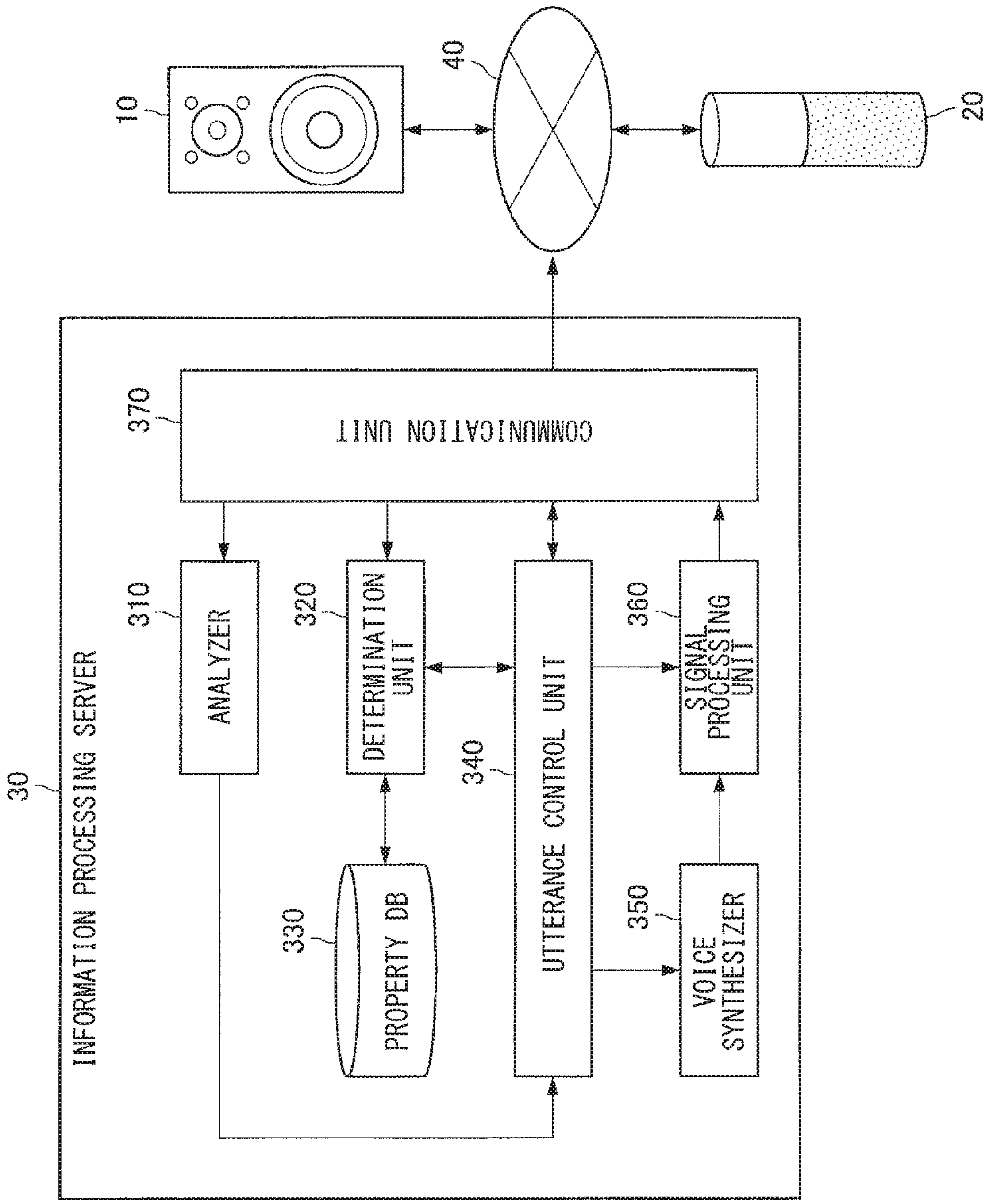
FIG. 5 is an example of a functional block diagram of an information processing server according to the embodiment.

Next, a functional configuration example of the information processing server 30 according to the present embodiment is described in detail. FIG. 5 is an example of a functional block diagram of the information processing server 30 according to the present embodiment. FIG. 5 illustrates that the information processing server 30 according to the present embodiment includes an analyzer 310, a determination unit 320, a property DB 330, an utterance control unit 340, a voice synthesizer 350, a signal processing unit 360, and a communication unit 370.

(Analyzer 310)

The analyzer 310 according to the present embodiment has a function of performing a background sound analysis on the basis of the background sound collected by the information processing terminal 20 and the information of content transmitted from the reproduction apparatus 10. Specifically, the analyzer 310 according to the present embodiment is able to analyze the voice quality, prosody, sound quality, main portion, and the like of the background sound. The analyzer 310 may then perform the analysis described above on the basis of a technique that is widely used in the field of sound analyzers.

(Determination Unit 320)

Figure 6:
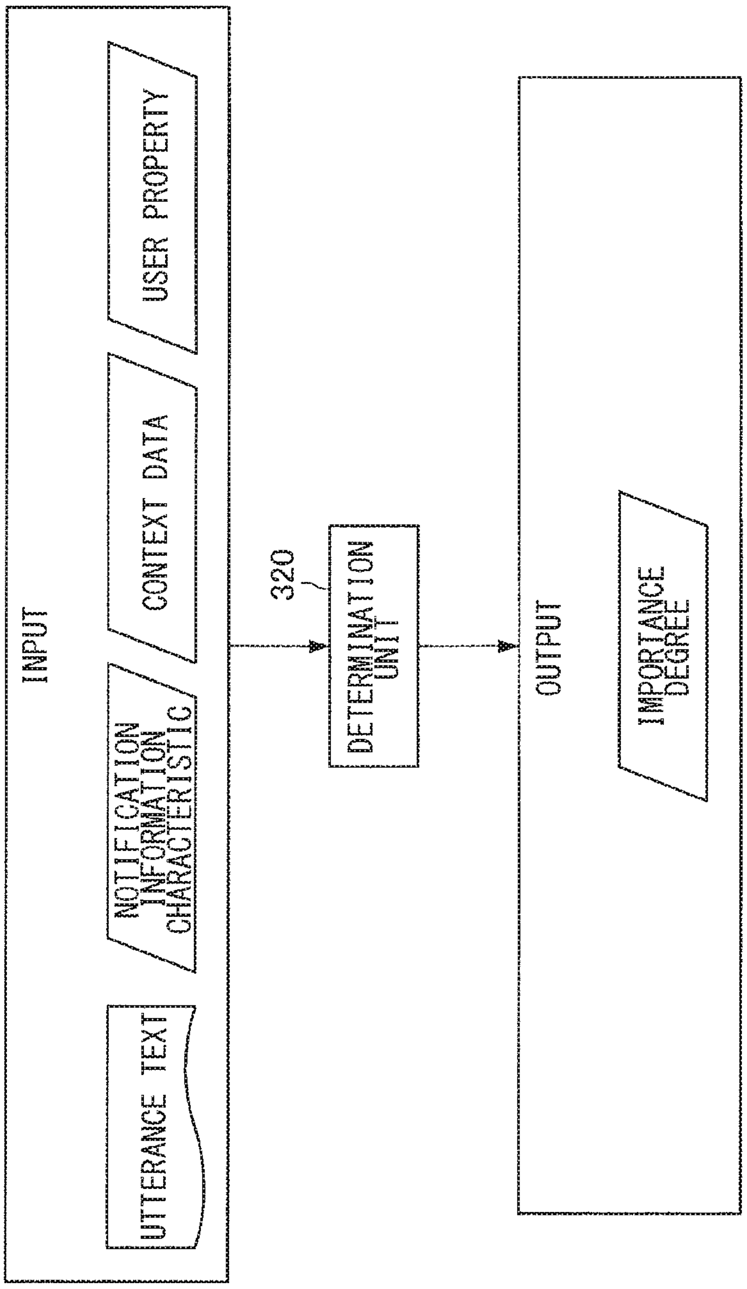
FIG. 6 is a diagram for describing a determination made by a determination unit according to the embodiment about an importance degree of notification information.

The determination unit 320 according to the present embodiment has a function of determining the importance degree of notification information. Note that the importance degree of notification information according to the present embodiment includes the urgency degree of a notification. FIG. 6 is a diagram for describing a determination made by the determination unit 320 according to the present embodiment about an importance degree of notification information. As illustrated in the diagram, the determination unit 320 according to the present embodiment is able to determine the importance degree of notification information on the basis of various kinds of inputted information.

Specifically, the determination unit 320 may determine the importance degree of notification information on the basis of utterance text indicating the contents of a spoken utterance, the characteristics of the notification information, context data for the notification information, the user property of a user to whom the notification information is presented, and the like.

Here, the above-described characteristics of notification information may include the contents and the class of the notification information. For example, in a case where the notification information is information that is distributed to a large number of unspecified users, for example, for reading aloud news, weather, advertisement, relevant information regarding content, or web information including SNS (social networking service), the determination unit 320 may determine that the importance degree of the notification information is relatively low. The notification information whose importance degree is determined by the determination unit 320 to be relatively low includes, in addition to the examples described above, various kinds of information that cause less damage even in a case where a user fails to hear the information, but bring benefits if the user selectively listens to the information.

In contrast, for example, in a case where notification information is information of which an individual user is notified such as schedule, a message, a response to an inquiry made by the user, and a navigation, the determination unit 320 may determine that the importance degree of the notification information is relatively high. The notification information whose importance degree is determined by the determination unit 320 to be relatively high includes, in addition to the examples described above, various kinds of information that may disadvantage a user in a case where the user fails to hear the information.

As described above, the determination unit 320 according to the present embodiment is able to determine the importance degree of notification information on the basis of the characteristics of the notification information. Note that the determination unit 320 may acquire the characteristics of notification information as exemplified above as metadata, or may acquire the metadata by analyzing utterance text.

In addition, even in a case where pieces of notification information have the same characteristics, it is assumed that some situations in which the pieces of notification information are outputted change the importance degrees of the pieces of notification information for a user. The determination unit 320 according to the present embodiment may therefore determine the importance degree of notification information on the basis of the context data for the information notification. Here, the context data described above refers to various kinds of information each indicating a situation in which notification information is outputted. The context data according to the present embodiment includes, for example, sensor information, utterance information, user schedule, and the like collected by the information processing terminal 20.

For example, in a case where notification information is information regarding the weather forecast of a spot A, the notification information normally has a relatively low importance degree. However, in a case where a user is scheduled to go to the spot A, the notification information is considered to temporarily have a high importance degree. In this case, the determination unit 320 is able to determine the importance degree of the notification information for the weather forecast of the spot A on the basis of context data such as the collected utterance information and schedule, and destination information inputted by the user.

In addition, it is assumed that some situations also change the importance degree of notification information for warning or alerting a user. For example, in a situation in which the vehicle approaches from behind, a situation in which a rapid increase in the user's temperature or blood pressure is detected, or the like in a case where the user is jogging while listening to music, the determination unit 320 may determine that the importance degree of notification information regarding the situation is high. The determination unit 320 is then able to make the determination described above on the basis of sensor information or the like collected by the information processing terminal 20 or another external apparatus. The above-described function of the determination unit 320 according to the present embodiment makes it possible to appropriately determine the importance degree of notification information in accordance with the situation, and perform the output control of the spoken utterance according to the importance degree.

In addition, it is assumed that the importance degree of notification information is not the same for all users, but is different for each user. The determination unit 320 according to the present embodiment may thus determine the importance degree of notification information on the basis of the user property regarding a user to whom the notification information is presented. Here, the user property described above includes the characteristics and tendencies of a user.

For example, in a case where notification information pertains to the delivery of news, but the news belongs to a category that a user frequently views, the determination unit 320 may determine that the importance degree of the notification information is high. In contrast, in a case where notification information pertains to the reception of a message, but a past tendency demonstrates that a user makes no reply or the message comes from a sender who replies late, the determination unit 320 may determine that the importance degree of the notification information is low.

It is assumed that the importance degree of notification information changes in accordance with the characteristics of the user such as sex, age, and place of residence. The determination unit 320 according to the present embodiment may therefore determine the importance degree of notification information on the basis of the characteristics as described above. The determination unit 320 according to the present embodiment is able to make the determination as exemplified above on the basis of the information of the user property held in the property DB 330. In this way, the above-described function of the determination unit 320 according to the present embodiment makes it possible to more flexibly determine an importance degree in accordance with the tendencies and characteristics of a user.

Note that the determination unit 320 according to the present embodiment may acquire an importance degree that is statically set in advance for notification information. Examples of the importance degree that is statically set in advance include information of an importance degree that is set by a sender when a message is sent, and an importance degree that is explicitly set by a user for the category or the like of notification information.

(Property DB 330)

The property DB 330 according to the present embodiment is a database that holds and accumulates information regarding the user property described above. Note that the property DB 330 may accumulate sensor information collected by the information processing terminal 20 or the like, feedback information from a user for the output of a spoken utterance, or the like, in addition to the information regarding the user property. The determination unit 320 is able to improve the determination accuracy by analyzing and learning various kinds of information accumulated by the property DB 330.

(Utterance Control Unit 340)

The utterance control unit 340 according to the present embodiment has a function of controlling the output of a spoken utterance corresponding to notification information. As described above, one of the characteristics of the utterance control unit 340 according to the present embodiment is to control the output mode of a spoken utterance by the information processing terminal 20 on the basis of the importance degree of notification information and the affinity for the background sound. A specific example of the control performed by the utterance control unit 340 according to the present embodiment is separately described in detail.

(Voice Synthesizer 350)

The voice synthesizer 350 according to the present embodiment has a function of synthesizing an artificial voice used for a spoken utterance on the basis of the control performed by the utterance control unit 340. The artificial voice generated by the voice synthesizer 350 is transmitted to the information processing terminal 20 via the communication unit 370 and the network 40, and is audibly outputted by the audio output unit 230.

(Signal Processing Unit 360)

The signal processing unit 360 according to the present embodiment executes various kinds of signal processing on the artificial voice synthesized by the voice synthesizer 350 on the basis of the control performed by the utterance control unit 340. For example, the signal processing unit 360 may perform processing of changing a sampling rate, processing of cutting a certain frequency component by a filter, processing of changing an SN ratio by noise superimposition, or the like.

(Communication Unit 370)

The communication unit 370 according to the present embodiment has a function of performing information communication with apparatuses such as the reproduction apparatus 10 and the information processing terminal 20 via the network 40. Specifically, the communication unit 370 receives a background sound, an utterance, sensor information, and the like from the information processing terminal 20 and the like. In addition, the communication unit 370 transmits an artificial voice synthesized by the voice synthesizer 350 and a control signal for the artificial voice to the information processing terminal 20. In addition, the communication unit 370 transmits a control signal for the cancellation processing on a singing voice or an utterance to the reproduction apparatus 10. The cancellation processing is described below.

The functional configuration example of the information processing server 30 according to the present embodiment has been described above in detail. Note that the functional configuration described above with reference to FIG. 5 is merely an example. The functional configuration of the information processing server 30 according to the present embodiment is not limited to the example. For example, the information processing server 30 according to the present embodiment may be implemented as the same apparatus as the reproduction apparatus 10 or the information processing terminal 20. It is possible to flexibly modify the functional configuration of the information processing server 30 according to the present embodiment in accordance with the specifications and operations.

<<1.6. Specific Example of Control>>

Next, the control performed by the information processing server 30 according to the present embodiment is described in detail with reference to a specific example.

(Specific Example of Output Mode Control)

First, a specific example of the output mode control according to the present embodiment is described. The utterance control unit 340 according to the present embodiment sets an output mode of high affinity for a background sound such as music on the basis that the determination unit 320 determines that the importance degree of notification information is relatively low. In contrast, the utterance control unit 340 sets an output mode of low affinity for a background sound on the basis that the determination unit 320 determines that the importance degree of notification information is relatively high.

FIG. 7 is a diagram illustrating an example of an output mode controlled by the utterance control unit 340 according to the present embodiment. FIG. 7 illustrates an example of a case where the utterance control unit 340 controls the voice quality, effects, and prosody of a spoken utterance on the basis of the importance degree of notification information. Note that FIG. 7 illustrates an example of control performed in a case where a speaker is set as a woman in her thirties who has a standard voice pitch, and a spoken utterance is outputted with high sound quality and at standard speed as the default settings.

In addition, FIG. 7 illustrates an example of a case where the speaker of a background sound is a man in his sixties who has a low voice pitch, and the sound quality of the background sound is low and the speed is low. The speaker described above may include, for example, a vocal in music, an utterer in video or the real world, and the like.

Here, in a case where the importance degree of notification information is relatively high, the utterance control unit 340 sets an output mode of low affinity for the background sound, thereby allowing a spoken utterance to stand out as compared with the background sound. Specifically, the utterance control unit 340 may set a speaker who has voice quality that is not similar to the voice quality of the speaker of the background sound. In the case of the example illustrated in FIG. 7, the utterance control unit 340 sets a woman in teens who has a high voice pitch, thereby offering voice quality of low affinity for the background sound. In addition, the utterance control unit 340 may emphasize a spoken utterance as compared with the background sound by performing control to cause the spoken utterance to be outputted with high sound quality and at high speed.

In contrast, in a case where the importance degree of notification information is relatively low, the utterance control unit 340 sets an output mode of high affinity for the background sound, thereby making it possible to make a spoken utterance that matches the background sound. Specifically, the utterance control unit 340 is able to set a speaker who has voice quality similar to the voice quality of the speaker of the background sound. In the case of the example illustrated in FIG. 7, the utterance control unit 340 sets the same man in his sixties who has a low voice as the speaker of the background sound, and causes a spoken utterance to be outputted that matches the background sound. Note that the utterance control unit 340 may not only set a speaker who has voice quality similar to that of the speaker of the background sound, but also learn, in advance, for example, the voice of the vocal, the favorite voice of a user, or the like, and perform control to cause a spoken utterance to be outputted with learned voice quality.

In addition, the utterance control unit 340 may make a spoken utterance match the background sound by performing control to cause the spoken utterance to be outputted with low sound quality and at low speed. The utterance control unit 340 is also able to control the sound quality of a spoken utterance in accordance with the production time, release time, and the like of music content. For example, in a case where music content collected as the background sound was produced a relatively long time ago, the utterance control unit 340 causes the signal processing unit 360 to limit the bandwidth of a spoken utterance or add noise. This makes it possible to cause the spoken utterance to be outputted with sound quality that matches the background sound.

As described above, the utterance control unit 340 according to the present embodiment sets a parameter for an output mode such as voice quality, effects, or prosody in accordance with the importance degree of notification information, and delivers the parameter to the voice synthesizer 350 and the signal processing unit 360. This allows the utterance control unit 340 according to the present embodiment to control the affinity of a spoken utterance for a background sound. In addition, as described above, the utterance control unit 340 according to the present embodiment may further control the output timing of a spoken utterance.

(Simultaneous Control Over Plurality of Spoken Utterances)

Figure 8:
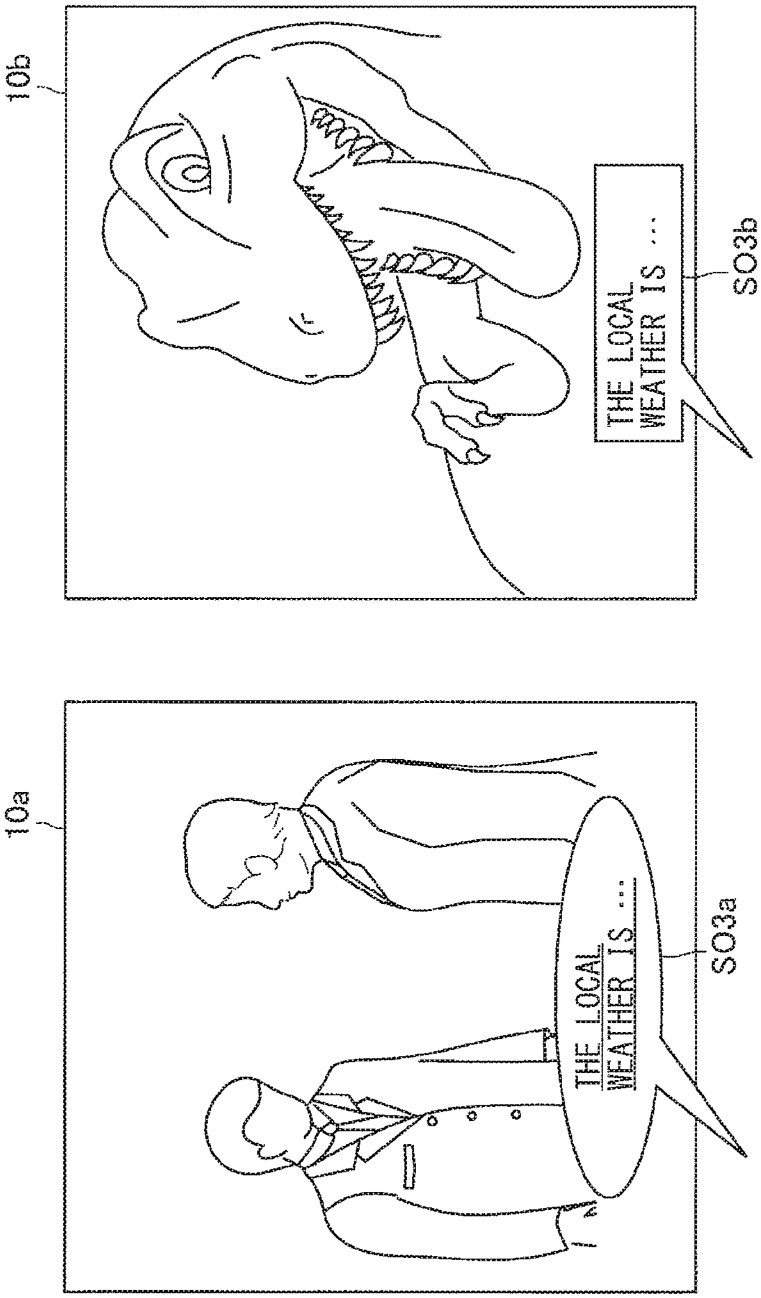
FIG. 8 is a diagram for describing simultaneous control performed by the utterance control unit according to the embodiment over a plurality of spoken utterances.

Next, the simultaneous control performed by the utterance control unit 340 according to the present embodiment over a plurality of spoken utterances is described. The utterance control unit 340 according to the present embodiment is also able to simultaneously control spoken utterances made by the plurality of information processing terminals 20. FIG. 8 is a diagram for describing the simultaneous control performed by the utterance control unit 340 according to the present embodiment over a plurality of spoken utterances.

FIG. 8 illustrates a situation in which, for example, different users use respective different reproduction apparatuses 10*a* and 10*b* to view and listen to respective pieces of video content in an airplane or the like. The utterance control unit 340 according to the present embodiment is then able to control the respective output modes of a plurality of spoken utterances SO3*a* and SO3*b* on the basis of the affinity of the importance degree of an in-flight announcement for the respective pieces of video content that are, in other words, background sounds.

For example, in a case where the in-flight announcement has a relatively low importance degree such as information regarding the weather of the destination, the utterance control unit 340 may control the respective output modes to cause the spoken utterances SO3*a* and SO3*b* to match the respective pieces of video content reproduced by the reproduction apparatuses 10*a* and 10*b*. In other words, the utterance control unit 340 is able to set the output mode of the spoken utterance SO3*a* to cause the spoken utterance SO3*a* to match the video content reproduced by the reproduction apparatus 10*a*, and set the output mode of the spoken utterance SO3*b* to cause the spoken utterance SO3*b* to match the video content reproduced by the reproduction apparatus 10*b*. The above-described function of the utterance control unit 340 makes it possible to issue, to each user, an appropriate information notification according to the situation even in the presence of the plurality of reproduction apparatuses 10 and information processing terminals 20.

(Control of Relevant Notification Matching Background Sound)

Next, the control of a relevant notification that matches a background sound according to the present embodiment is described. The utterance control unit 340 according to the present embodiment sets an output mode to cause notification information to match a background sound in a case where the notification information is related to the details of content for the background sound. This also allows the utterance control unit 340 according to the present embodiment to issue a more natural information notification.

Figure 9:
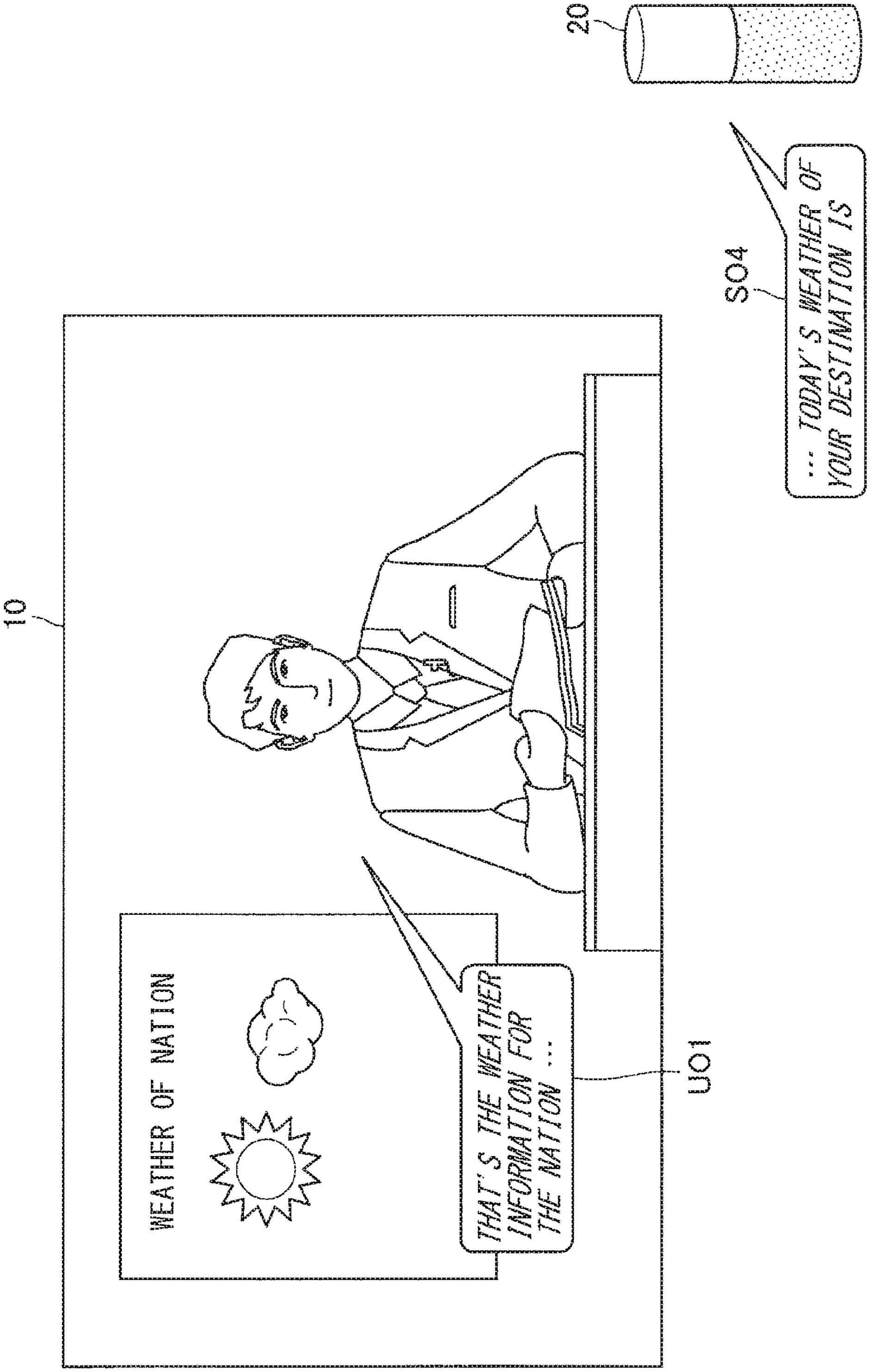
FIG. 9 is a diagram for describing control of a relevant notification that matches a background sound according to the embodiment.

FIG. 9 is a diagram for describing the control of a relevant notification that matches a background sound according to the present embodiment. FIG. 9 illustrates a situation in which a broadcasting program regarding the weather forecast of the nation is reproduced by the reproduction apparatus 10. The utterance control unit 340 according to the present embodiment is then able to cause a spoken utterance SO4 to match the background sound, and cause the spoken utterance SO4 to be outputted. The spoken utterance SO4 pertains to the weather of the place of a user's residence held in the property DB 330 or the destination of a user acquired as schedule information. Specifically, the utterance control unit 340 causes the spoken utterance SO4 to be outputted following an utterance UO1 of the newscaster in the broadcasting program described above. This allows the utterance control unit 340 to issue an information notification without making a strange impression as if the information for the individual user were announced by the newscaster. Voice quality similar to that of the utterance UO1 is set for the spoken utterance SO4.

(Control of Output Mode for Affinity for Environmental Sound)

Next, the control of an output mode for the affinity for an environmental sound according to the present embodiment is described. As described above, the background sound according to the present embodiment includes an environmental sound. The utterance control unit 340 according to the present embodiment is able to perform the control of an output mode that takes into consideration the affinity for the background sound.

Figure 10:
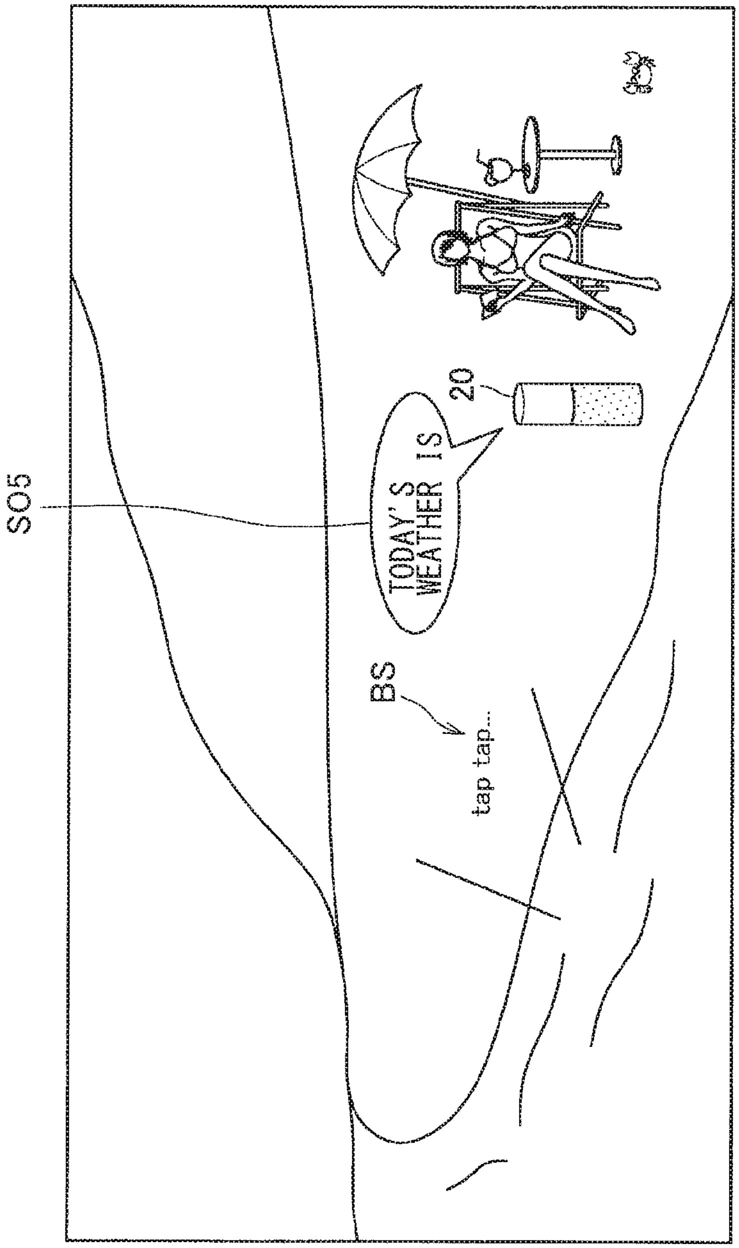
FIG. 10 is a diagram for describing control of an output mode for affinity for an environmental sound according to the embodiment.

FIG. 10 is a diagram for describing the control of an output mode for the affinity with the environmental sound according to the present embodiment. FIG. 10 illustrates an example of a case where the utterance control unit 340 causes the information processing terminal 20 to output a spoken utterance SO5 for notification information of a relatively low urgency degree when a user is relaxing on the beach.

The utterance control unit 340 according to the present embodiment may then set an output mode of high affinity for the background sound BS that is the sound of the waves collected by the information processing terminal 20, and cause the spoken utterance SO5 to be outputted. The utterance control unit 340 is able to cause the spoken utterance SO5 to be outputted, for example, with voice quality that matches the pitch of the sound of the waves or with prosody that matches the rhythm of the waves.

The above-described function of the utterance control unit 340 according to the present embodiment makes it possible to cause a spoken utterance to be outputted in an appropriate output mode according to an environmental sound. For example, it is possible to issue an information notification that does not spoil the mood of a user who is on vacation. Note that FIG. 10 illustrates an example of a case where the environmental sound is the sound of the waves, but the environmental sound according to the present embodiment includes, for example, various sounds such as a chirping bird or insect, the sound of rain or wind, the sound of a firework, the sound generated as a vehicle progresses, and the sound of crowds.

(Control of Output Mode for Affinity for Background Sound in Game)

Next, the control of an output mode for the affinity for the background sound in a game according to the present embodiment is described. The background sound according to the present embodiment includes, for example, various sounds outputted in a game. Therefore, the utterance control unit 340 according to the present embodiment may set an output mode for a spoken utterance by taking the affinity for a sound as described above into consideration.

Figure 11:
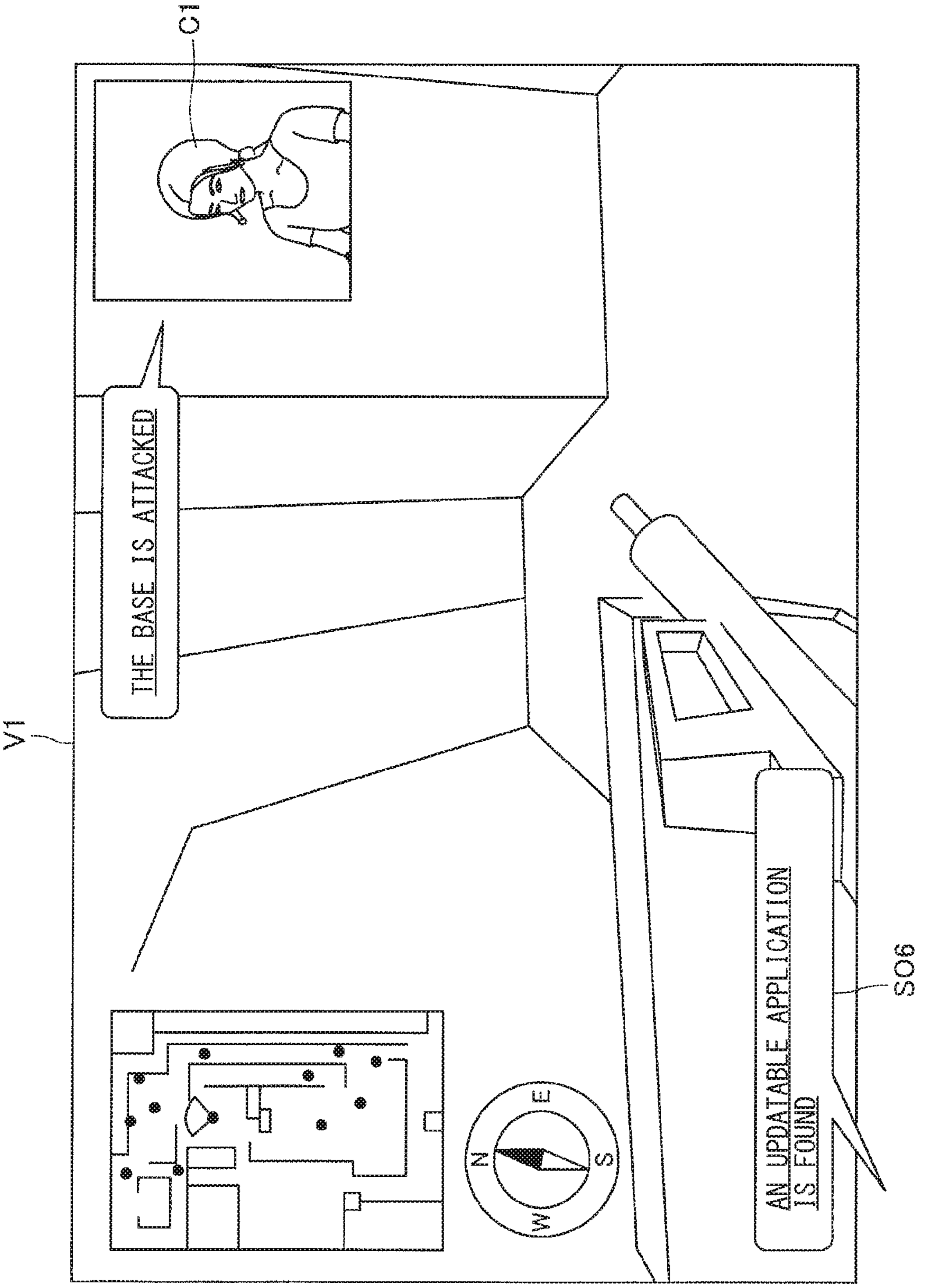
FIG. 11 is a diagram for describing control of an output mode for affinity for a background sound in a game according to the embodiment.

FIG. 11 is a diagram for describing the control of an output mode for the affinity for the background sound in the game according to the present embodiment. FIG. 11 exemplifies a visual field V1 of a user who is wearing the reproduction apparatus 10, and playing a survival game for which AR (Augmented Reality) or VR (virtual reality) technology is used. The reproduction apparatus 10 is an eyeglass type wearable apparatus or a head-mounted wearable apparatus.

The utterance control unit 340 according to the present embodiment is then able to set an output mode that takes into consideration the affinity for a voice or the like emitted by a character C1 such as a navigator in the game, and cause a spoken utterance SO6 to be outputted. Specifically, in a case where the importance degree of notification information is relatively low, the utterance control unit 340 causes the spoken utterance SO6 to be outputted with voice quality similar to that of the character C1. This makes it possible to issue an information notification that matches the background sound.

The utterance control unit 340 is then able to cause the voice synthesizer 350 to synthesize an artificial voice having voice quality similar to that of the character C1 on the basis of a parameter for the voice quality of the character C1 received by the communication unit 370. In this way, the communication unit 370 according to the present embodiment may receive a parameter for an output mode from the reproduction apparatus 10 or the like. Note that the above-described parameter for an output mode includes the parameter for voice quality, effects, prosody, or the like exemplified in FIG. 7.

(Control of Spoken Utterance Accompanied by Cancellation Processing on Singing Voice, Utterance, or Like)

Next, the control of an output mode accompanied by cancellation processing on a singing voice, an utterance, or the like according to the present embodiment is described. The utterance control unit 340 according to the present embodiment cancels a portion of a background sound, thereby making it possible to issue an information notification that matches the background sound more. Specifically, the utterance control unit 340 is able to cause a singing voice, an utterance, or the like included in the background sound to be cancelled, and simultaneously cause a spoken utterance to be outputted in an output mode similar to that of the singing voice, the utterance, or the like.

Figure 12:
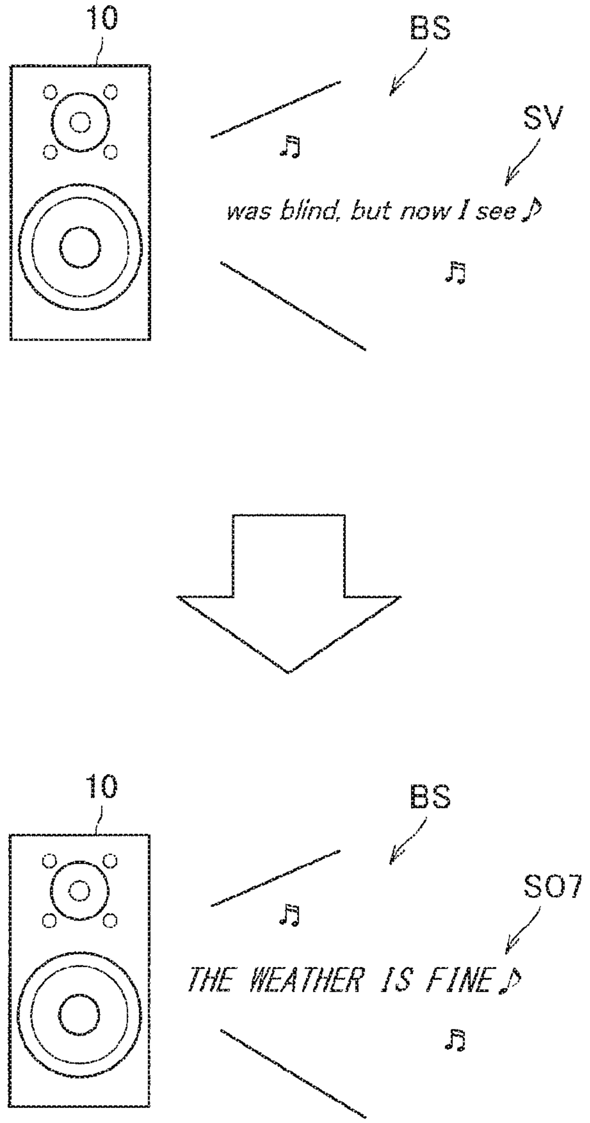
FIG. 12 is a diagram for describing control of an output mode accompanied by cancellation processing on a singing voice, an utterance, or the like according to the embodiment.

FIG. 12 is a diagram for describing the control of an output mode accompanied by the cancellation processing on a singing voice, an utterance, or the like according to the present embodiment. In the case of the example illustrated in FIG. 12, the utterance control unit 340 causes a singing voice SV to be cancelled in the background sound BS that is music reproduced by the reproduction apparatus 10, and causes a spoken utterance SO7 to be outputted. The spoken utterance SO7 has an output mode similar to that of the singing voice SV. In other words, the utterance control unit 340 is able to synthesize a singing voice corresponding to notification information with voice quality, prosody, and effects similar to those of the singing voice SV, and cause the singing voice to be outputted as the spoken utterance SO7.

The above-described function of the utterance control unit 340 according to the present embodiment makes it possible to issue an information notification that matches a background sound such as music more, and effectively attract the interest of a user.

<<1.7. Flow of Control>>

Figure 13:
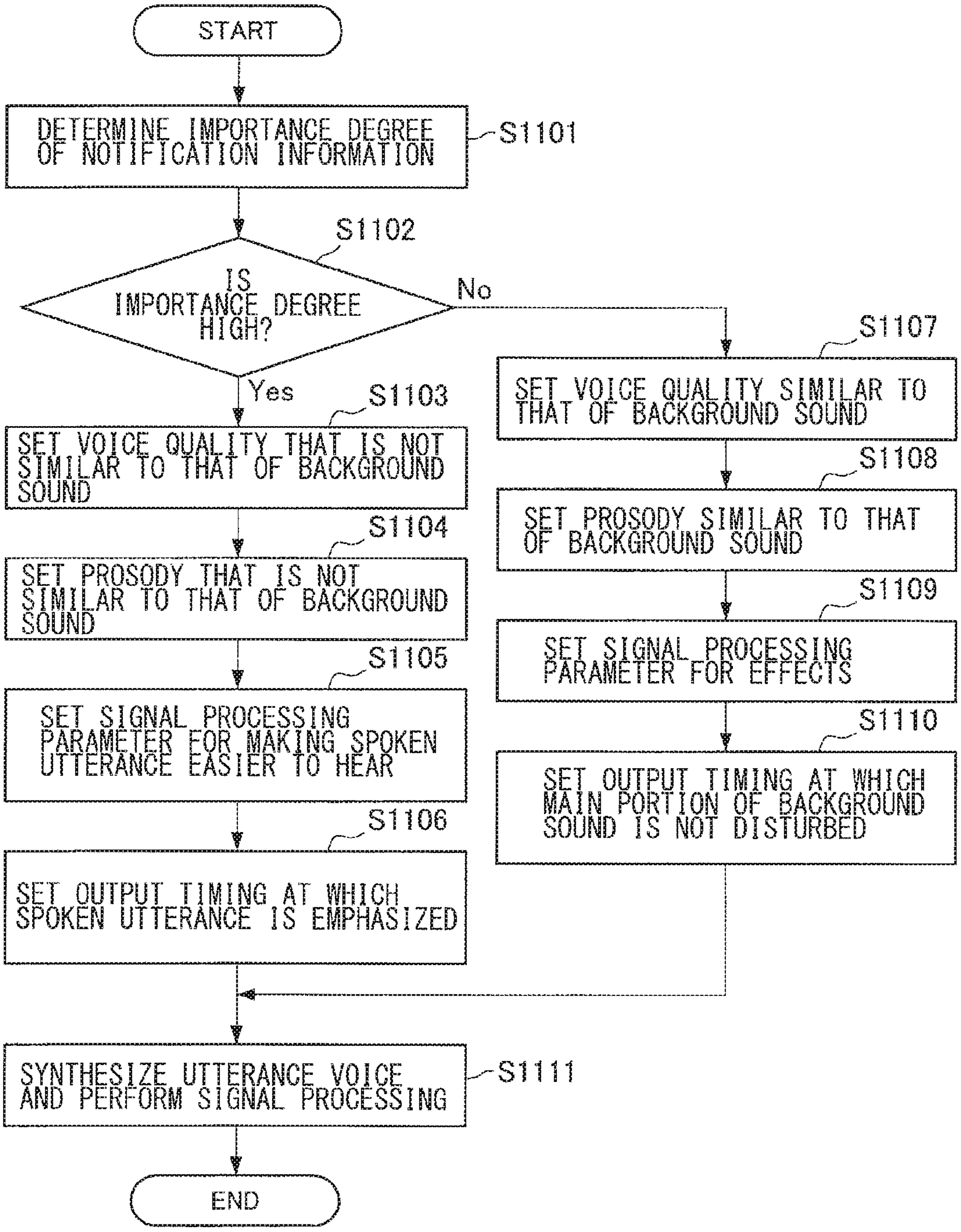
FIG. 13 is a flowchart illustrating a flow of control performed by an information processing server according to the embodiment.

Next, the flow of the control performed by the information processing server 30 according to the present embodiment is described in detail. FIG. 13 is a flowchart illustrating the flow of the control performed by the information processing server 30 according to the present embodiment.

FIG. 13 illustrates that the determination unit 320 first determines the importance degree of notification information (S1101).

In a case where the determination unit 320 determines here that the importance degree of the notification information is high (S1102: Yes), the utterance control unit 340 sets voice quality that is not similar to that of the collected background sound (S1103).

In addition, the utterance control unit 340 sets prosody that is not similar to that of the background sound (S1104).

In addition, the utterance control unit 340 may set a parameter for signal processing to emphasize a spoken utterance as compared with the background sound, or make the spoken utterance easier to hear (S1105).

In addition, the utterance control unit 340 sets output timing at which the spoken utterance is emphasized as compared with the background sound (S1106)

In contrast, in a case where the determination unit 320 determines that the importance degree of the notification information is not high (S1102: No), the utterance control unit 340 sets voice quality similar to that of the collected background sound (S1107).

In addition, the utterance control unit 340 sets prosody similar to that of the background sound (S1108).

In addition, the utterance control unit 340 sets a parameter for signal processing to attain effects similar to those of the background sound (S1109).

In addition, the utterance control unit 340 sets output timing at which the main portion of the background sound is not disturbed (S1110).

Subsequently, the voice synthesizer 350 and the signal processing unit 360 synthesize an artificial voice and perform signal processing on the basis of the parameters for the output mode set in steps S1103 to 1110, and the artificial voice and the control signal are transmitted to the information processing terminal 20.

2. Example of Hardware Configuration

Figure 14:
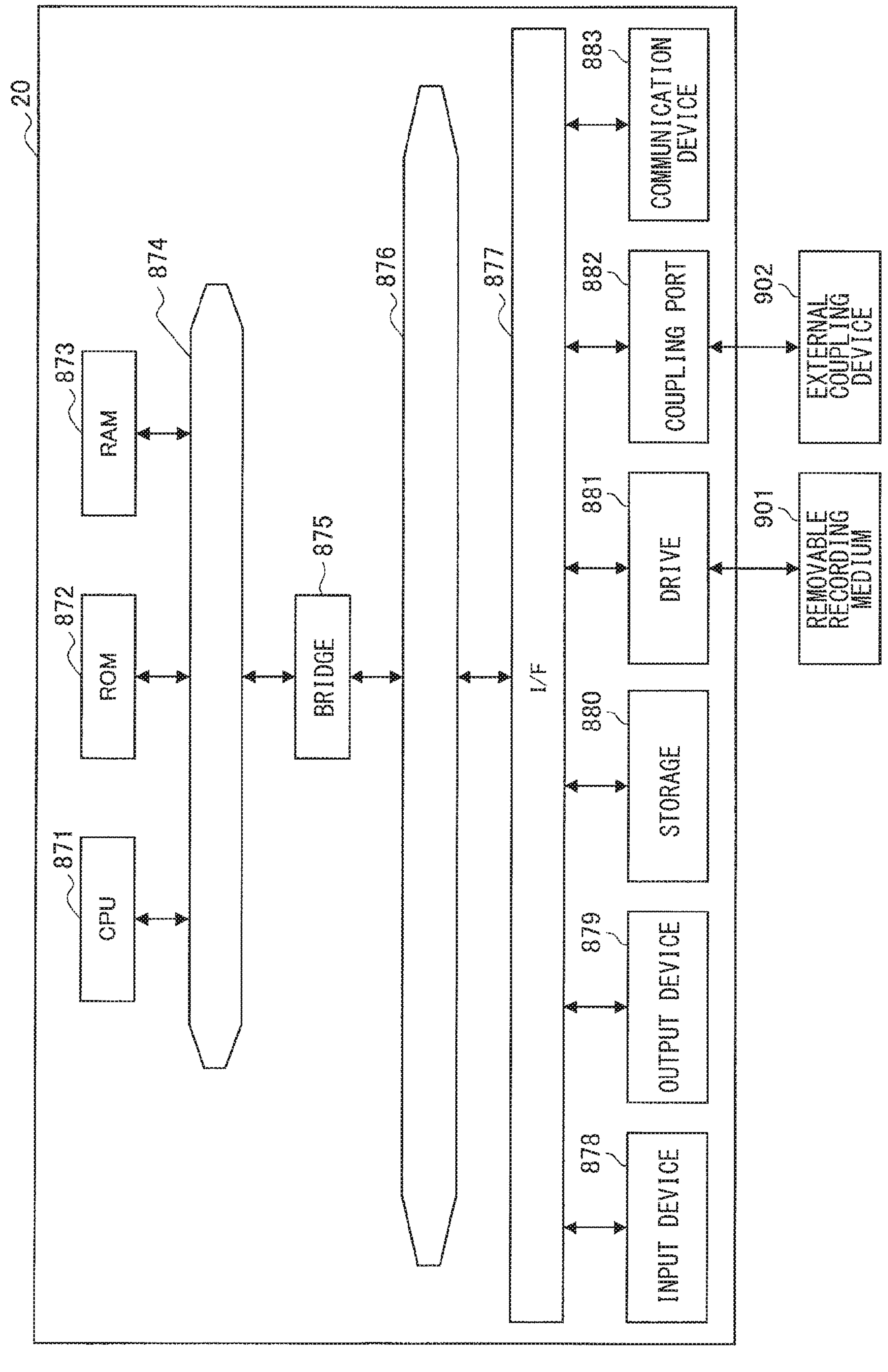
FIG. 14 is a diagram illustrating an example of a hardware configuration according to an embodiment of the present disclosure.

Next, an example of the hardware configuration common to the reproduction apparatus 10, information processing terminal 20, and information processing server 30 according to an embodiment of the present disclosure is described. FIG. 14 is a block diagram illustrating an example of the hardware configurations of the reproduction apparatus 10, information processing terminal 20, and information processing server 30 according to an embodiment of the present disclosure. FIG. 14 illustrates that the reproduction apparatus 10, information processing terminal 20, and the information processing server 30 each includes, for example, a CPU 871, a ROM 872, a RAM 873, a host bus 874, a bridge 875, an external bus 876, an interface 877, an input device 878, an output device 879, a storage 880, a drive 881, a coupling port 882, and a communication device 883. Note that the hardware configuration illustrated here is an example, and a portion of the components may be omitted. In addition, a component other than the components illustrated here may be further included.

(CPU 871)

The CPU 871 functions as, for example, an arithmetic processing device or a control device, and controls all or a portion of the operations of each component on the basis of various programs recorded in the ROM 872, the RAM 873, the storage 880, or a removable recording medium 901.

(ROM 872 and RAM 873)

The ROM 872 is a means for storing a program to be read by the CPU 871, data to be used for operation, or the like. The RAM 873 temporarily or permanently stores, for example, a program to be read by the CPU 871, various parameters appropriately changing in executing the program, or the like.

(Host Bus 874, Bridge 875, External Bus 876, and Interface 877)

The CPU 871, the ROM 872, and the RAM 873 are coupled to each other, for example, via the host bus 874 that is able to transmit data at high speed. Meanwhile, the host bus 874 is coupled to the external bus 876 having a relatively low data transmission rate, for example, via the bridge 875. In addition, the external bus 876 is coupled to various components via the interface 877.

(Input Device 878)

For example, a mouse, a keyboard, a touch panel, a button, a switch, a lever, and the like are used for the input device 878. Further, as the input device 878, a remote controller (referred to as remote control below) is sometimes used that is able to transmit a control signal by using infrared rays or other radio waves. In addition, the input device 878 includes a voice input device such as a microphone.

(Output Device 879)

The output device 879 is a device that is able to visually or aurally notify a user of acquired information. Examples of the device include a display device such as a CRT (Cathode Ray Tube), an LCD, or an organic EL, an audio output device such as a speaker or a headphone, a printer, a mobile phone, a facsimile, and the like. In addition, the output device 879 according to the present disclosure includes various vibration devices that are able to output tactile stimulation.

(Storage 880)

The storage 880 is a device for storing various kinds of data. As the storage 880, for example, a magnetic storage device such as a hard disk drive (HDD), a semiconductor storage device, an optical storage device, a magneto-optical storage device, or the like is used.

(Drive 881)

The drive 881 is, for example, a device that reads out information recorded in the removable recording medium 901 such as a magnetic disk, an optical disc, a magneto-optical disk, or a semiconductor memory, or writes information to the removable recording medium 901.

(Removable Recording Medium 901)

The removable recording medium 901 includes, for example, a DVD medium, a Blu-ray (registered trademark) medium, an HD DVD medium, various semiconductor storage media, and the like. Needless to say, the removable recording medium 901 may be, for example, an IC card, an electronic device, or the like each of which is mounted with a contactless IC chip.

(Coupling Port 882)

The coupling port 882 is, for example, a port for coupling an external coupling device 902 such as a USB (Universal Serial Bus) port, an IEEE 1394 port, SCSI (Small Computer System Interface), an RS-232C port, or an optical audio terminal.

(External Coupling Device 902)

The external coupling device 902 is, for example, a printer, a portable music player, a digital camera, a digital video camera, an IC recorder, or the like.

(Communication Device 883)

The communication device 883 is a communication device for coupling to a network. The communication device 883 is, for example, a communication card for wired or wireless LAN, Bluetooth (registered trademark), or WUSB (Wireless USB), a router for optical communication, a router for ADSL (Asymmetric Digital Subscriber Line), a modem for various kinds of communication, or the like.

3. Summary

As described above, the information processing server 30 according to an embodiment of the present disclosure has a function of controlling the output mode of a spoken utterance on the basis of the importance degree of notification information to change the affinity for a background sound. According to the configuration, it is possible to more flexibly control the affinity of a spoken utterance for a background sound in accordance with the importance degree of an information notification.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

In addition, the respective steps for the processes of the information processing server 30 in this specification are not necessarily performed in chronological order in accordance with the order illustrated in the flowchart. For example, the respective steps for the processes of the information processing server 30 may be performed in order different from the order illustrated in the flowchart, or may also be performed in parallel.

Note that the technical scope of the present disclosure also includes the following configurations.

(1)

An information processing apparatus including an utterance control unit that controls an output of a spoken utterance corresponding to notification information, the utterance control unit controlling an output mode of the spoken utterance on the basis of an importance degree of the notification information and affinity for a background sound.

(2)

The information processing apparatus according to (1), in which the output mode includes at least one of output timing, voice quality, prosody, or an effect of the spoken utterance.

(3)

The information processing apparatus according to (1) or (2), in which the utterance control unit sets the output mode of high affinity for the background sound on the basis that the importance degree of the notification information is determined to be low, and causes the spoken utterance to be outputted.

(4)

The information processing apparatus according to any of (1) to (3), in which the utterance control unit sets voice quality similar to voice quality for the background sound on the basis that the importance degree of the notification information is determined to be low, and causes the spoken utterance to be outputted.

(5)

The information processing apparatus according to any of (1) to (4), in which the utterance control unit sets prosody similar to prosody for the background sound on the basis that the importance degree of the notification information is determined to be low, and causes the spoken utterance to be outputted.

(6)

The information processing apparatus according to any of (1) to (5), in which the utterance control unit sets sound quality similar to sound quality for the background sound on the basis that the importance degree of the notification information is determined to be low, and causes the spoken utterance to be outputted.

(7)

The information processing apparatus according to any of (1) to (6), in which the utterance control unit sets output timing at which a main portion included in the background sound is not disturbed, on the basis that the importance degree of the notification information is determined to be low, and causes the spoken utterance to be outputted.

(8)

The information processing apparatus according to any of (1) to (7), in which the utterance control unit sets a singing voice adapted to the background sound, on the basis that the importance degree of the notification information is determined to be low, and causes the singing voice to be outputted.

(9)

The information processing apparatus according to any of (1) to (8), in which the utterance control unit sets the output mode of low affinity for the background sound on the basis that the importance degree of the notification information is determined to be high, and causes the spoken utterance to be outputted.

(10)

The information processing apparatus according to any of (1) to (9), in which the utterance control unit sets voice quality that is not similar to voice quality for the background sound, on the basis that the importance degree of the notification information is determined to be high, and causes the spoken utterance to be outputted.

(11)

The information processing apparatus according to any of (1) to (10), in which the utterance control unit sets prosody that is not similar to prosody for the background sound, on the basis that the importance degree of the notification information is determined to be high, and causes the spoken utterance to be outputted.

(12)

The information processing apparatus according to any of (1) to (11), in which the utterance control unit sets sound quality that is not similar to sound quality for the background sound, on the basis that the importance degree of the notification information is determined to be high, and causes the spoken utterance to be outputted.

(13)

The information processing apparatus according to any of (1) to (12), in which the utterance control unit sets output timing at which the spoken utterance is emphasized as compared with the background sound, on the basis that the importance degree of the notification information is determined to be high, and causes the spoken utterance to be outputted.

(14)

The information processing apparatus according to any of (1) to (13), in which the background sound includes at least one of music, an utterance, or an environmental sound.

(15)

The information processing apparatus according to any of (1) to (14), further including a determination unit that determines the importance degree of the notification information.

(16)

The information processing apparatus according to (15), in which the determination unit determines the importance degree of the notification information on the basis of context data for the notification information.

(17)

The information processing apparatus according to (15) or (16), in which the determination unit determines the importance degree of the notification information on the basis of user property regarding a user to whom the notification information is presented.

(18)

The information processing apparatus according to any of (15) to (17), in which the determination unit determines the importance degree of the notification information on the basis of a characteristic of the notification information.

(19)

The information processing apparatus according to any of (1) to (18), further including a communication unit that receives a parameter for the output mode.

(20)

An information processing method including controlling, by a processor, an output of a spoken utterance corresponding to notification information, the controlling further including controlling an output mode of the spoken utterance on the basis of an importance degree of the notification information and affinity for a background sound.

REFERENCE NUMERALS LIST

10 reproduction apparatus
110 reproduction unit
120 processing unit
130 communication unit
20 information processing terminal
210 audio input unit
220 sensor unit
230 audio output unit
240 communication unit
30 information processing server
310 analyzer
320 determination unit
330 property DB
340 utterance control unit
350 voice synthesizer
360 signal processing unit
370 communication unit

The invention claimed is:

1. An information processing apparatus comprising circuitry configured to analyze a background sound;

control an output of a spoken utterance corresponding to notification information, the notification information being information to be issued through a spoken utterance as an information notification;

determine an importance degree of the notification information to be a first importance degree or a second importance degree;

determine an affinity for the background sound based on the importance degree, a first affinity corresponding to the first importance degree and a second affinity corresponding to the second importance degree; and control an output mode of the spoken utterance on a basis of the affinity for the background sound, the control including simultaneously cancelling a first portion of the background sound and, on condition that the affinity is the first affinity, match the spoken utterance to that of the cancelled first portion and, on condition that the affinity is the second affinity, make the spoken utterance stand out from that of the cancelled first portion; and output a second portion of the background sound and the spoken utterance in the first portion of the background sound.

2. The information processing apparatus according to claim 1, wherein the circuitry is configured to match the spoken utterance or make the spoken utterance stand out includes controlling at least one of output timing, voice quality, prosody, or an effect of the spoken utterance.

3. The information processing apparatus according to claim 1, wherein the circuitry is configured to set, on condition that the affinity is the second affinity, voice quality similar to voice quality for the background sound.

4. The information processing apparatus according to claim 1, wherein the circuitry is configured to, on condition that the affinity is the second affinity, set prosody similar to prosody for the background sound.

5. The information processing apparatus according to claim 1, wherein the circuitry is configured to, on condition that the affinity is the second affinity, set sound quality similar to sound quality for the background sound.

6. The information processing apparatus according to claim 1, wherein the circuitry is configured to, on condition that the affinity is the second affinity, set output timing at which a main portion included in the background sound is not disturbed.

7. The information processing apparatus according to claim 1, wherein the circuitry is configured to, on condition that the affinity is the second affinity, set a singing voice adapted to the background sound.

8. The information processing apparatus according to claim 1, wherein the circuitry is configured to, on condition that the affinity is the first affinity, set voice quality that is not similar to voice quality for the background sound.

9. The information processing apparatus according to claim 1, wherein the circuitry is configured to, on condition that the affinity is the first affinity, set prosody that is not similar to prosody for the background sound, on a basis that the importance degree of the notification information is determined to be high, and causes the spoken utterance to be outputted.

10. The information processing apparatus according to claim 1, wherein the circuitry is configured to, on condition that the affinity is the first affinity, set sound quality that is not similar to sound quality for the background sound.

11. The information processing apparatus according to claim 1, wherein the circuitry is configured to, on condition that the affinity is the first affinity, set output timing at which the spoken utterance is emphasized as compared with the background sound.

12. The information processing apparatus according to claim 1, wherein the background sound includes at least one of music, an utterance, or an environmental sound.

13. The information processing apparatus according to claim 1, wherein the circuitry is configured to determine the importance degree of the notification information on a basis of user property regarding a user to whom the notification information is presented.

14. The information processing apparatus according to claim 1, wherein the circuitry is configured to determine the importance degree of the notification information on a basis of a characteristic of the notification information.

15. The information processing apparatus according to claim 1, further comprising a communication unit that receives circuitry is configured to output a parameter for the output mode.

16. An information processing method comprising, by a processor, analyzing a background sound;

controlling an output of a spoken utterance corresponding to notification information, the notification information being information to be issued through a spoken utterance as an information notification;

determining an importance degree of the notification information to be a first importance degree or a second importance degree;

determining an affinity for the background sound based on the importance degree, a first affinity corresponding to the first importance degree and a second affinity corresponding to the second importance degree; and controlling an output mode of the spoken utterance on a basis of the affinity for the background sound, controlling of the output mode including simultaneously cancelling a first portion of the background sound and, on condition that the affinity is the first affinity, match the spoken utterance to that of the cancelled first portion and, on condition that the affinity is the second affinity, make the spoken utterance stand out from that of the cancelled first portion; and outputting a second portion of the background sound and the spoken utterance in the first portion of the background sound.

17. The information processing method according to claim 16, wherein matching the spoken utterance or making the spoken utterance stand out includes controlling at least one of output timing, voice quality, prosody, or an effect of the spoken utterance.

18. The information processing method according to claim 16, further comprising, on condition that the affinity is the second affinity, setting at least one of a voice quality, prosody, and output timing that is similar to voice quality, prosody, and output timing for the background sound.

19. The information processing method according to claim 16, further comprising, on condition that the affinity is the first affinity, setting at least one of a voice quality, prosody, and output timing that is different from voice quality, prosody, and output timing for the background sound.

20. The information processing method according to claim 16, further comprising determining the importance degree of the notification information on a basis of at least one of a user property regarding a user to whom the notification information is presented and a characteristic of the notification information.

* * * * *